United States Patent
Sakai et al.

(10) Patent No.: US 7,806,262 B2
(45) Date of Patent: Oct. 5, 2010

(54) CONTAINER

(75) Inventors: Masazumi Sakai, Suita (JP); Katsunori Fujita, Mobara (JP); Shingo Sakamoto, Osaka (JP); Ryoichi Nishikawa, Osaka (JP)

(73) Assignee: Bayer Schering Pharma AG, Berlin (DE)

( * ) Notice: Subject to any disclaimer, the term of this patent is extended or adjusted under 35 U.S.C. 154(b) by 355 days.

(21) Appl. No.: 11/704,676

(22) Filed: Jul. 10, 2006

(65) Prior Publication Data
US 2007/0158234 A1   Jul. 12, 2007

(30) Foreign Application Priority Data

Jan. 10, 2006  (JP)  .............................. 2006-000256
Jan. 10, 2006  (JP)  .............................. 2006-000257

(51) Int. Cl.
*B65D 83/10*  (2006.01)

(52) U.S. Cl. .................... 206/366; 206/370; 206/443

(58) Field of Classification Search ................ 206/488, 206/363–367, 438, 528, 485, 521, 591, 748–750, 206/571, 362.4, 564; 229/165, 120.13, 117.17, 229/120.18, 407, 920, 930
See application file for complete search history.

(56) References Cited

U.S. PATENT DOCUMENTS

| | | | | |
|---|---|---|---|---|
| 2,833,457 A | * | 5/1958 | Tyrseck | ...................... 206/763 |
| 3,115,247 A | * | 12/1963 | Hauser | ........................ 206/528 |
| 3,133,635 A | * | 5/1964 | Gordon et al. | .............. 206/366 |
| 3,305,084 A | * | 2/1967 | Higgins et al. | .............. 206/366 |
| 4,324,357 A | * | 4/1982 | Murkowski | ................. 206/521 |
| 4,523,679 A | * | 6/1985 | Paikoff et al. | ................ 206/370 |
| 4,739,881 A | * | 4/1988 | Bruso | ......................... 206/305 |
| 5,402,889 A | * | 4/1995 | Hermann et al. | ............ 206/443 |
| 5,429,243 A | * | 7/1995 | Woelk et al. | ................ 206/538 |
| 5,577,614 A | * | 11/1996 | Palmeroni et al. | ........... 206/521 |
| 6,296,121 B1 | * | 10/2001 | Hershey | ...................... 206/701 |
| 2003/0217944 A1 | * | 11/2003 | Belloli et al. | ............... 206/443 |
| 2006/0022023 A1 | * | 2/2006 | Kuenstler et al. | ...... 229/120.13 |

* cited by examiner

*Primary Examiner*—Mickey Yu
*Assistant Examiner*—Jenine M Pagan
(74) *Attorney, Agent, or Firm*—Millen, White, Zelano & Branigan, P.C.

(57) ABSTRACT

A package has a rectangular parallelepiped container including vertical front and rear panel sections connected by a pair of vertical side panel sections, a top wall connected to the upper edge of the rear panel section and a bottom wall connected to the at least one of the lower edges of the vertical panels and a top cushion panel disposed beneath the top wall and rotatably connected to at least one upper edge of the side panel sections. A holder is disposed, in the container, for holding a plurality of glass syringes each of which is sealingly contained in a plastic bag.

8 Claims, 6 Drawing Sheets

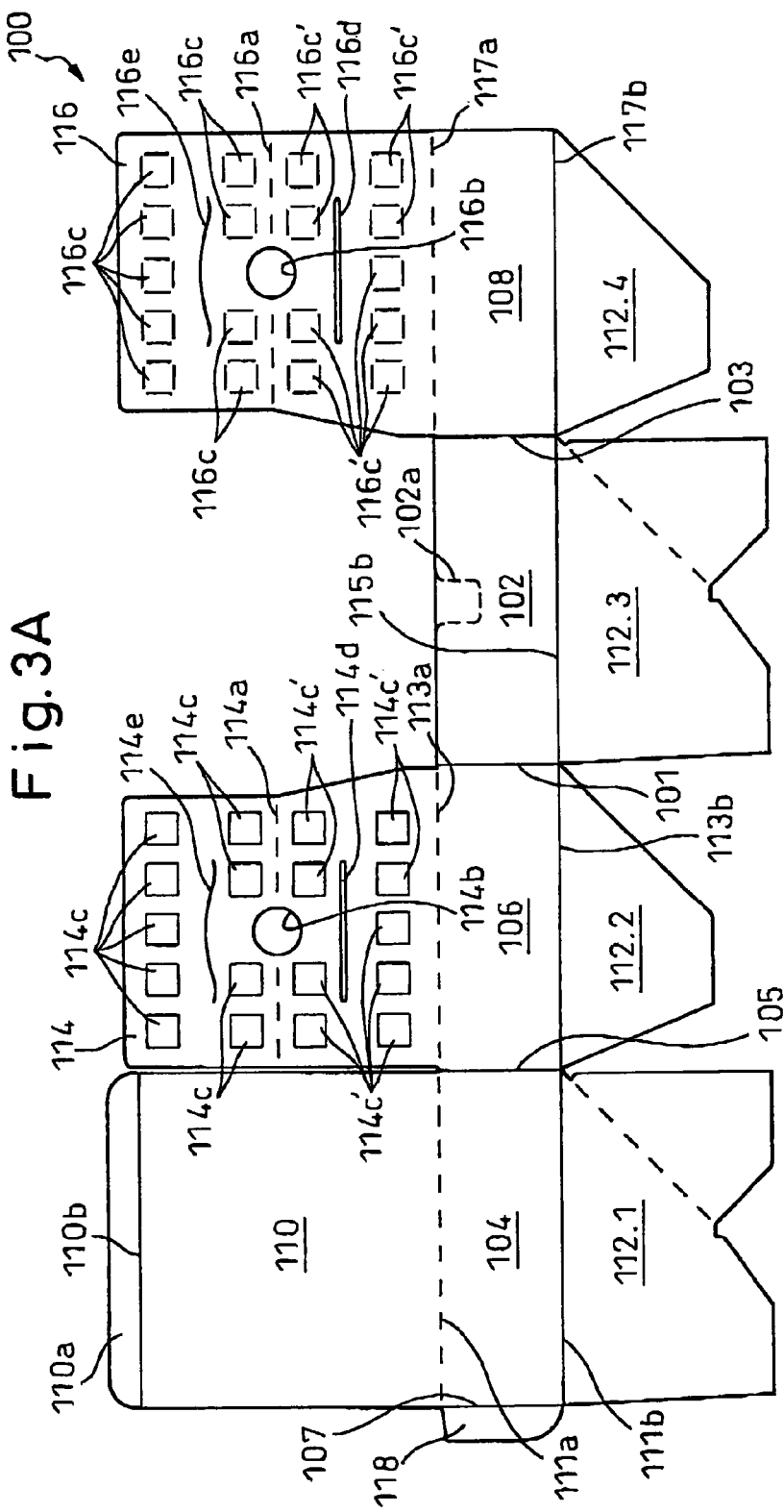
Fig.3A
Fig.3B

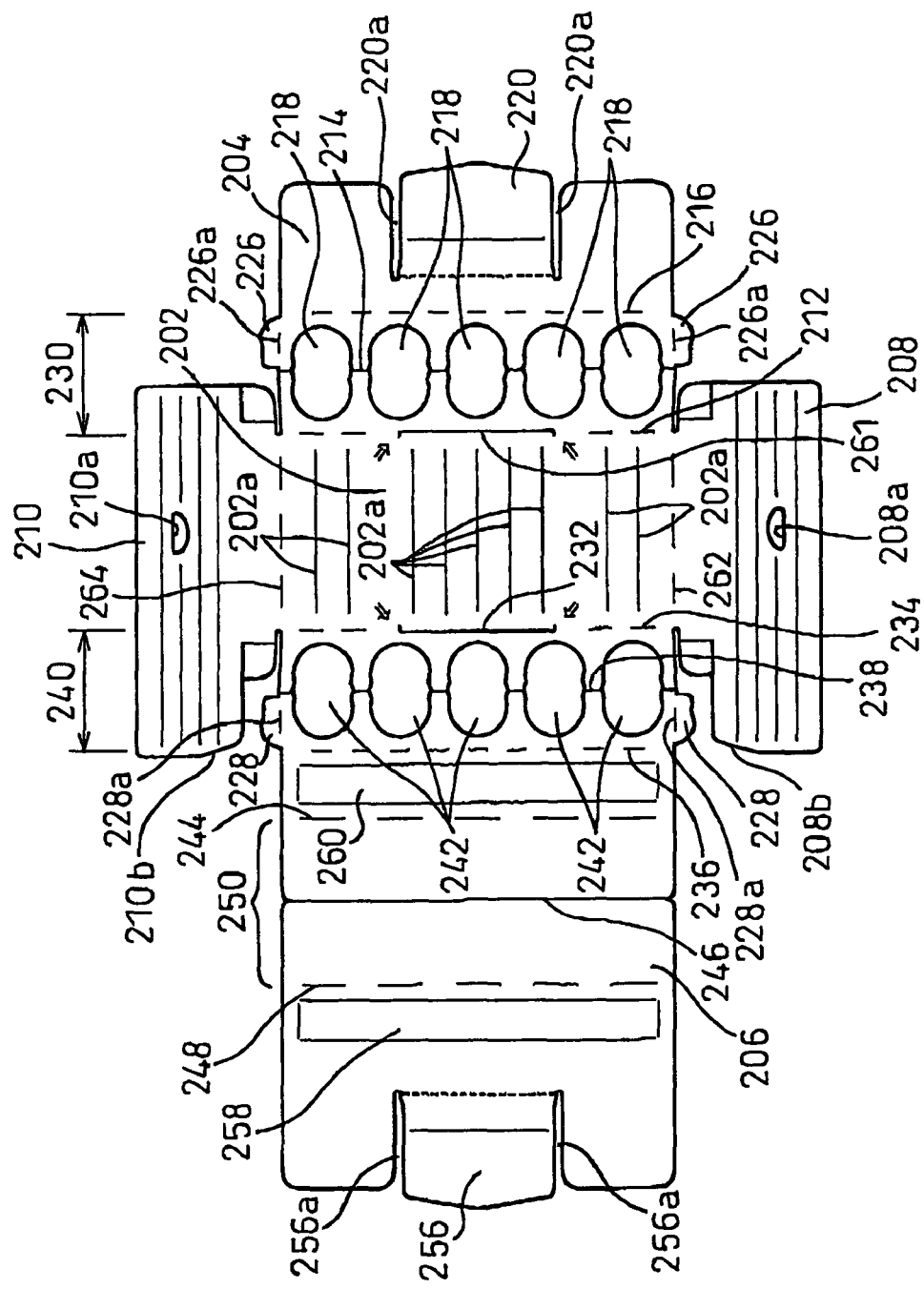

CONTAINER

BACKGROUND OF THE INVENTION

1. Field of the Invention

The invention relates to a container for a plurality of glass syringes containing a medical solution and a holder for securely holding and supporting the glass syringes within the container.

2. Description of the Related Art

Some medical solutions, such as contrast agents, are distributed as a glass syringe in which the medical solution is filled. A plurality of such glass syringes are commonly contained in a container for shipping and storage. In order to hold and support the syringes in the container, the glass syringes have been held by a plastic holder which can damp a shock applied to the container.

Recently, when a used has been discarded, segregation of the materials is required due to environment concerns. Further, plastic holders take much space for storage until they are brought to a waste disposer. Thus, plastic holders are gradually being replaced with holders made of corrugated board.

A container and holder of corrugated board have a good damping function to protect the glass syringes against a shock. However, corrugated board is thicker compared with a plain cardboard, resulting in a larger container and a larger holder. On the other hand, a smaller package is desirable considering the production, shipping and storing the package and, therefore, a smaller container and/or a smaller holder is required.

SUMMARY OF THE INVENTION

The invention is directed to solve the above mentioned prior art problems, an the objective of the invention is to provide a compact container for a plurality of glass syringes which has good damping effect against shock.

According to the present invention, there is provided a package which comprises a rectangular parallelepiped container including vertical front and rear panel sections connected by a pair of vertical side panel sections, top wall connected to the upper edge of the rear panel section and bottom wall connected to the at least one of the lower edges of the vertical panels and a top cushion panel disposed beneath the top wall and rotatably connected to at least one upper edge of the side panel sections, a plurality of glass syringes each of which is sealingly contained in a plastic bag, and a holder, disposed in the container, for holding the plurality of glass syringes substantially parallel to the top and bottom walls.

DESCRIPTION OF THE DRAWINGS

These and other objects and advantages and further description will now be discussed in connection with the drawings in which:

FIG. 3A is a plan view of a blank for forming the container of FIG. 2;

FIG. 3B is a partially enlarged plan view of an arcuate cut in a side flap of the blank of FIG. 3A;

FIG. 5 is a plan view of a blank for forming the holder of FIG. 4A.

DESCRIPTION OF THE PREFERRED EMBODIMENTS

With reference to the drawings, a preferred embodiment of the invention will be described below.

Figure 1A:
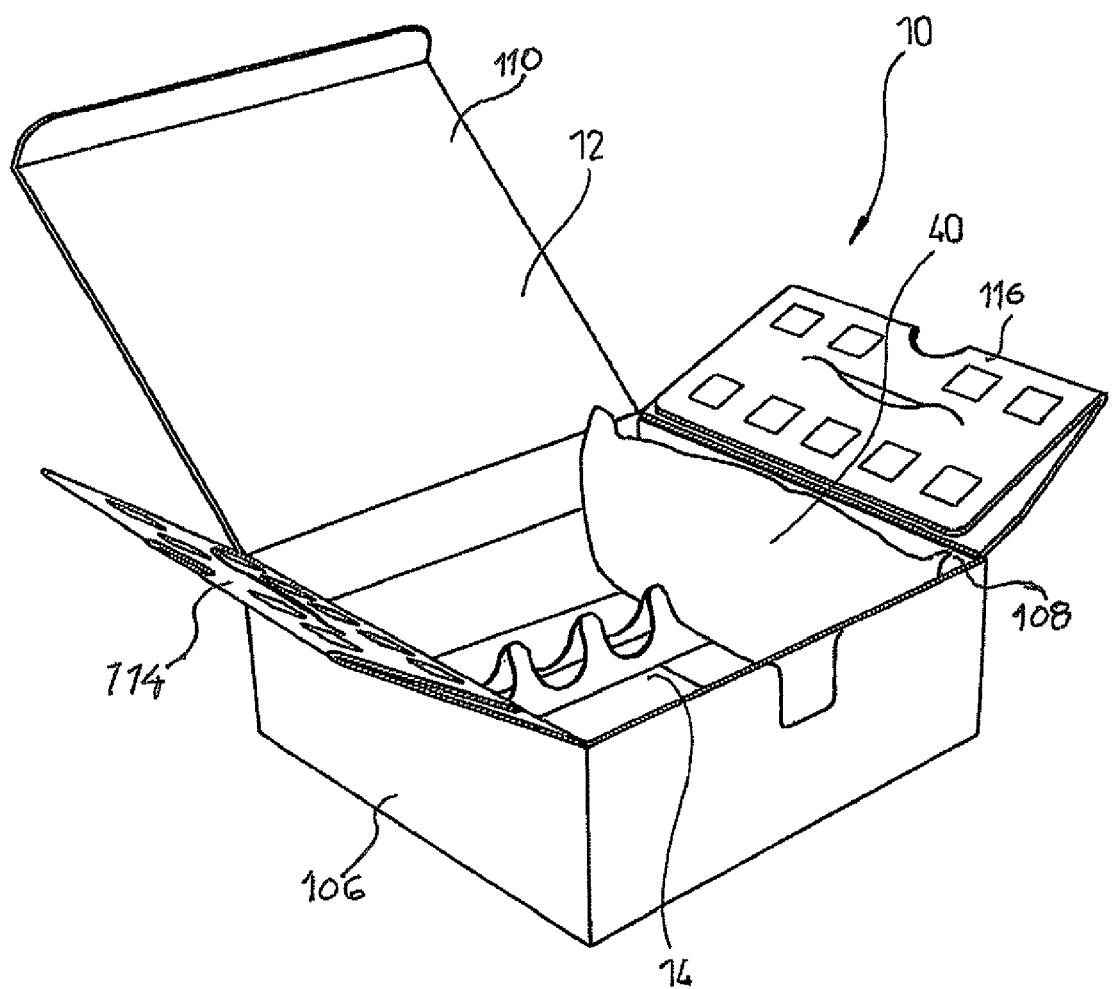
FIG. 1A is a perspective view of a package according to an embodiment of the invention in which the package is shown with a container opening.

With reference to FIG. 1A, a package 10 according to an embodiment of the present invention comprises a rectangular parallelepiped container 12, a holder 14 disposed in the container 12 for holding a plurality of glass syringes 20 (in FIG. 1B) sealingly contained in plastic bags 40.

Figure 1B:
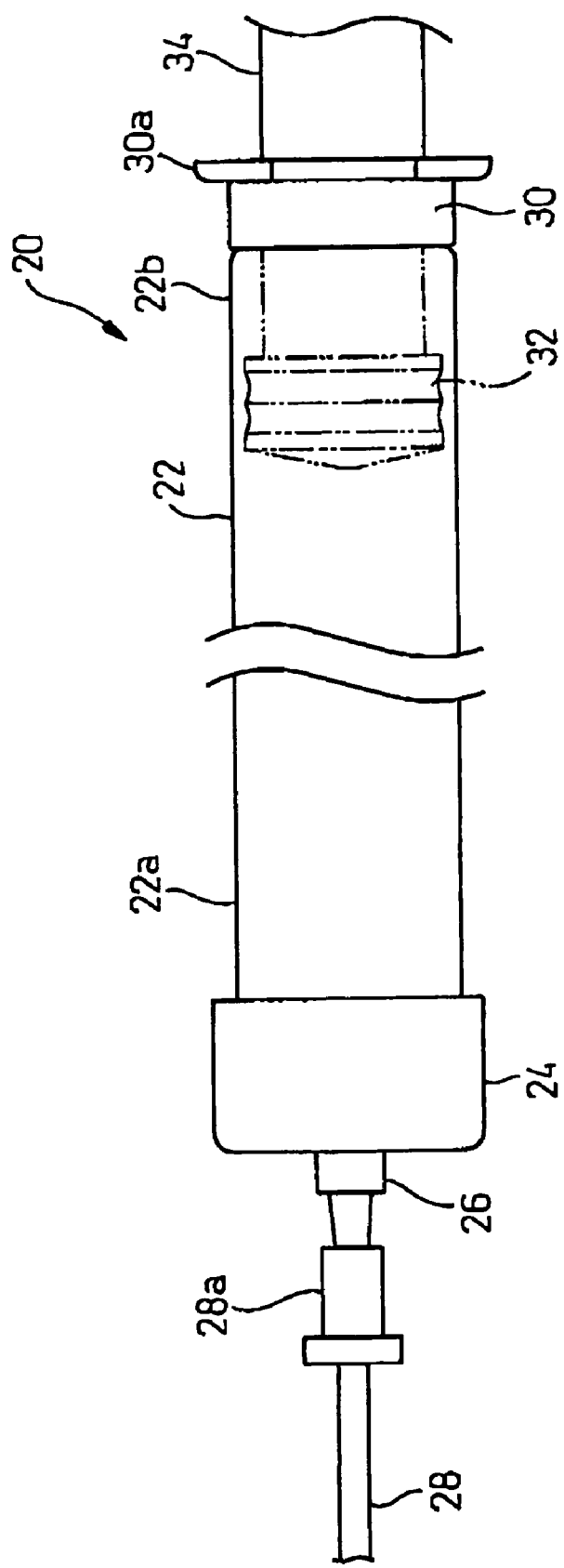
FIG. 1B is a longitudinal section of a glass syringe.

FIG. 1B shows an example of the glass syringe 20. In FIG. 1B, the glass syringe 20 comprises a hollow cylindrical body 22 for accommodating a medical solution such as a contrast agent. The syringe body 22 has a distal end portion 22a and a proximal end portion 22b. A lure lock lid 26 is mounted and secured to the distal end portion 22a by a lure lock holder 24. In FIG. 1B, only the tip, defining an inner cylinder (not shown) having an exit opening (not shown), of the lure lock lid 26 is shown. Before the glass syringe is used, a rubber plug (not shown) has been attached to the tip to sealingly close the exit opening, and a plastic cover is put over the rubber plug and the tip. When used, the rubber plug and the plastic cover are removed, and a tube 28 is attached to the tip of the lure lock lid 26 by a lure lock plug 28a. A flanged cap 30, defining a flange 30a, is attached to the proximal end portion 22b. The proximal end opening is sealingly closed by a piston 32. The piston 32 typically includes an inside threading for engagement with an outside threading of a piston rod 34. The detailed configuration of the glass syringe 20 is described in U.S. Pat. No. 5,782,815, the disclosure of which is incorporated herewith by reference.

Figure 2:
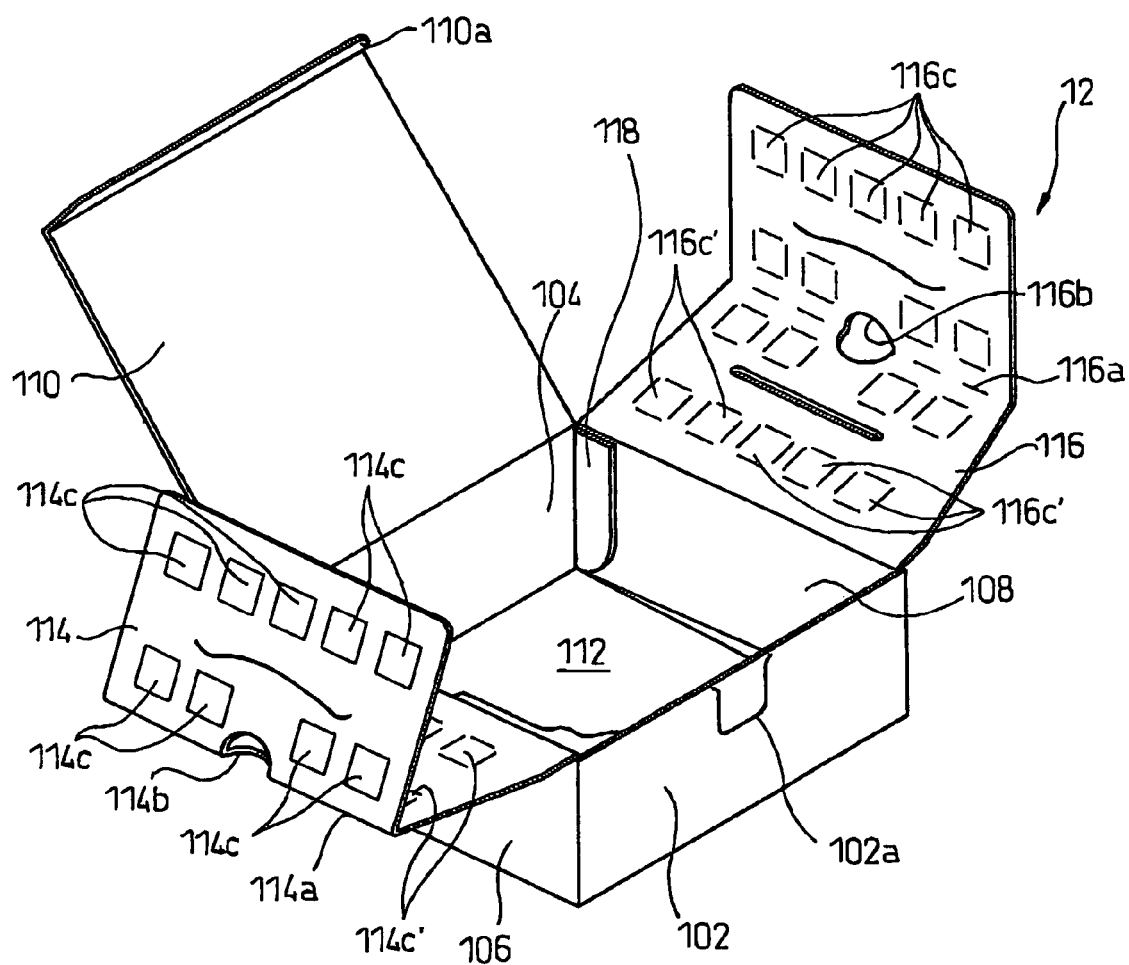
FIG. 2 is a perspective view of the container shown in FIG. 1A.

With reference to FIG. 2, the container 12 comprises front and rear panel sections 102 and 104, which are connected by a pair of side panel sections 106 and 108, and top and bottom walls 110 and 112. The front panel section 102 may include a perforation line 102a to provide an opening to facilitate the access to the top wall 110 when the container 12 is opened.

With reference to FIG. 3A, a blank 100 for forming the container 12 comprises a front panel section 102, a rear panel section 104, side panel sections 106 and 108 and an overlap section 118 for the attachment to the inner face of the side panel section 108 by glue. The side panel section 106 is foldably connected to one edge of the front panel section 102 by a vertical folding line 101, and to one edge of the rear panel section 104 by a vertical folding line 105. The side panel section 108 is foldably connected to the other edge of the front panel section 102 by a vertical folding line 103. The overlap section 118 is foldably connected to the other edge of the rear panel section 104 by a vertical folding line 107.

A top flap 110, providing the top wall or the cover 110, is foldably connected to an upper edge of the rear panel section 104 by an upper horizontal folding line 111a. The top flap 110 has an insertion section 110a connected to the leading edge of the top flap 110 by a folding line 110b. Bottom flaps 112.1 to 112.4, adapted to be incorporated with each other to provide the bottom wall 112, are foldably connected to lower edges of the rear, side, front and side panel sections 104, 106, 102 and 108 respectively by bottom horizontal folding lines 111b, 113b, 115b and 117b.

A pair of side flaps 114 and 116 are foldably connected to upper edges of the side panel sections 106 and 108 respectively by upper horizontal folding lines 113a and 117a. The side flap 114 includes a central folding line 114a extending parallel to the folding line 113a, a central hole 114b disposed on the center of the folding line 114a and a plurality of reliefs 114c and 114c' which are symmetrically disposed about the folding line 114a. The side flap 114 further includes a slot 114d and an arcuate cut 114e for providing a tang portion 114f (FIG. 3B) adapted to be inserted into the slot 114d. The side flap 116, likewise the side flap 114, includes a central folding line 116a extending parallel to the folding line 117a, a central hole 116b disposed on the center of the folding line 116a and a plurality of reliefs 116c and 116c' which are symmetrically disposed about the folding line 116a. The side flap 116 further includes a slot 116d and an arcuate cut 116e for providing a tang portion 116f (FIG. 3B) adapted be inserted into the slot 116e.

When formed into the container 12, the blank 100 is folded along vertical folding lines 107, 105, 101 and 103 so that the font and rear panels 102 and 104 face to each other, the side panels face to each other and the overlap section 118 contact the inner surface of the side panel section 108. The overlap section 118 is secured to the side panel section 108 by bonding means such as glue or an adhesive tape.

The bottom flaps 112.1 to 112.4 are folded along the bottom horizontal folding lines 111b, 113b, 115b and 117b and are incorporated with each other to provide the bottom wall 112.

The top flap 110 is folded relative to the rear panel section 104 along the upper horizontal folding line 111a to provide the top wall 110. The top flap 110 is further folded inwardly along the folding line 110b to provide the insertion section 110a which is adapted to be inserted between the top wall 110 and the front panel section 102.

The side flaps 114 and 116 are folded relative to the side panel sections 106 and 108 along the upper horizontal folding lines 113a and 117a. The side flaps 114 and 116 are further folded along the central folding lines 114a and 116a so that the reliefs 114c, and 116c are vertically aligned to the corresponding reliefs 114c' and 116c' to provide a double-walled top cushion panel. When the side flaps 114 and 116 are folded along the central folding lines 114a and 116a, the holes 114b and 116b provide semicircular halves of an access hole for facilitating the opening of the top cushion panel. After folded along the central folding lines 114a and 116a, the tang portions 114f and 116f are inserted into the slots 114d and 116d to secure the side flaps 114 and 116 to be folded along the central folding lines 114a and 116a.

Figure 4A:
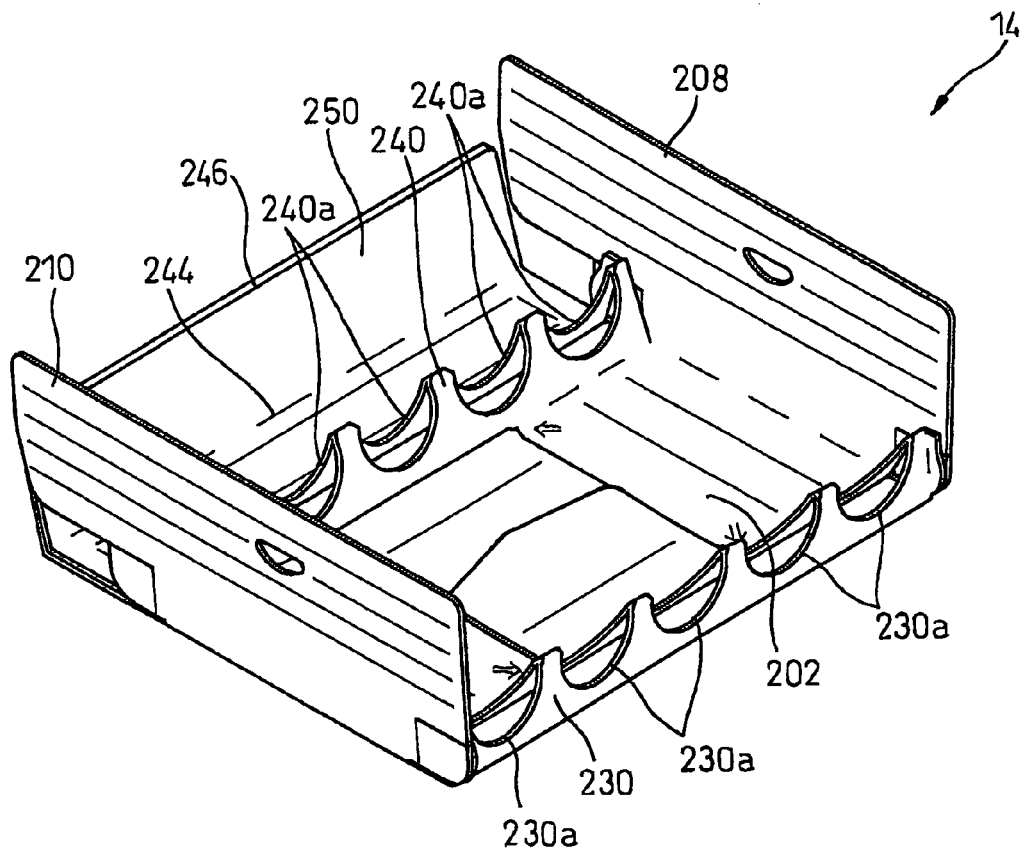
FIG. 4A is a perspective view of a holder for holding glass syringes according to an embodiment of the invention.

With reference to FIG. 4A, the holder 14 includes a bottom panel 202, front and rear side supports 230 and 240 disposed at the ends of the bottom panel 202, side panels 206 and 208 and a cushion panel 250.

With reference to FIG. 5, a blank 200 for forming the holder 14 includes a bottom panel section 202, a front flap 204 foldably connected to the bottom panel section 202 by a front folding line 212, a rear flap 206 foldably connected to the bottom panel section 202 by a rear folding line 234 parallel to the front folding line 212, a pair of side flaps 208 and 210 foldably connected to the bottom panel section 202 by parallel side folding lines 262 and 264, respectively. The bottom panel section 202 includes a plurality of dent lines 202a, which extend parallel to the side folding lines 262 and 264, for increasing the strength of the bottom panel 202 against the pressure in the front-rear direction applied to the bottom panel section 202 when the blank 200 is converted into the holder 14. The bottom panel section 202 further includes a pair of cuts 262 and 238 aligned with the front and rear folding lines 212 and 234.

The front flap 204 includes first and second folding lines 214 and 216 parallel to the front folding line 212, a plurality of apertures 218 laterally aligned with each other along the first folding line 214, a tang portion 220 defined in the marginal region by a pair of slits 220a and 220b and a pair of supporting tabs 226 foldably connected to the edges of front flap 204 by folding lines 226a.

The portion in the front flap 204 between the front folding line 212 and the second folding line 216 provides a front side support 230, when the blank 200 is formed into the holder 14, in the form of a ridge having a substantially a triangle section. The triangular section of the front side support 230 has a good shock-damping effect and provides morphologic stability enabling the front side support 230 to securely hold and support relatively heavy glass syringes without a change in its shape.

Figure 4B:
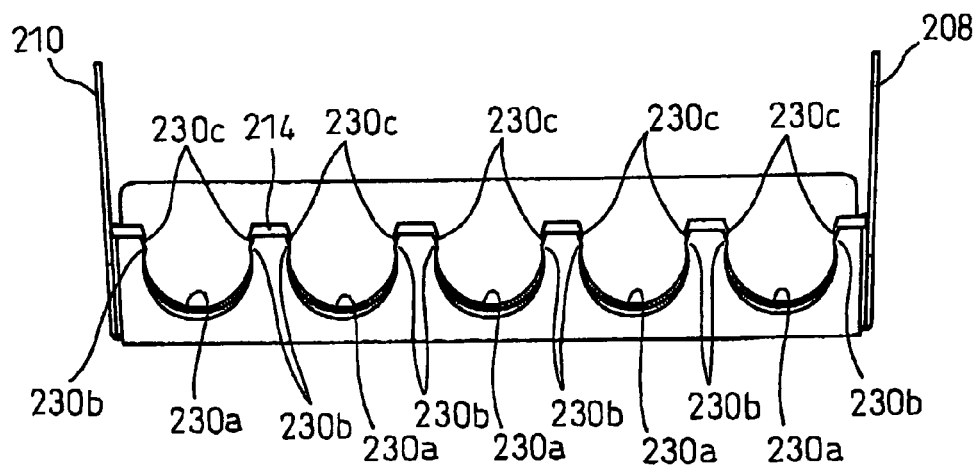
FIG. 4B is a front view of the holder of FIG. 4A.

With reference to FIG. 4B, the front side support 230 of the holder 14 includes a plurality of front receiving recesses 230a, for receiving and holding proximal end portion 22b of the syringe body 22, provided by the apertures 218, when the front flap 204 is folded along the first holding line 214. Each of the receiving recesses 230a has a substantially a semi-circular shape except that the receiving recess 230a has a pair of inwardly projecting lugs 230b, disposed adjacent the top opening of the recess, for engaging with a syringe body 22 inserted in the receiving recess. Each pair of the lugs 230b defines tapered surfaces 230c outwardly diverging relative to each other to facilitate the insertion of the syringe body 22 into the recess.

The rear flap 206 includes first to fifth folding lines 238, 236, 244, 246 and 248, a plurality of apertures 242 laterally aligned with each other along the first folding line 238, a tang portion 256 defined in the marginal region by a pair of slits 256a, back-side embosses 258 and 260, a pair of supporting tabs 228 foldably connected to the edges of the rear flap 206 by folding lines 228a.

The portion between the rear folding line 234 and the second folding lien 236 provide a rear side support 240, when the holder 14 is formed, in the form of a ridge having a substantially a triangle section. The triangular section of the support 240 has a good shock-damping effect and provides morphologic stability enabling the support 240 to securely hold and support relatively heavy glass syringes without a change in its shape. The rear side support 240 includes a plurality of rear receiving recesses 240a, provided by the apertures 242, for receiving and holding distal end portion 22a of the syringe body 22. The rear receiving recesses 240a have the configuration similar to those of the front receiving recesses 230a of the front side support 230. The front and rear receiving recesses are aligned with each other.

The portion between the third and fifth folding lines 244 and 248 provides a cushion panel 250 which is disposed between the rear panel 104 and the tips 26 of glass syringes 20 held by the holder 14 to damp a shock transmitted to the tips 26 of the glass syringe 20.

The back-side embosses 258 and 260 are raised to the back side (opposite to the surface of FIG. 5) of the blank 200 and are symmetrically disposed about the fourth folding line 246 so that the back-side embosses 258 and 260 contact with, and are secured to, each other by bonding means such as glue or an adhesive tape to provide the holder with morphologic stability when the holder 14 is formed.

When formed into the holder 14, the front flap 204 is folded along the front folding line 212 and the first and folding lines 214 and 216 to form the front side support 230 and to insert the tang portion 220 into the cut 262 from the back side of the blank 200. Likewise, the rear flap 206 is folded along the rear folding line 234 and the first to fifth folding lines 238, 236, 244, 246 and 248 to form the rear side support 240, to erect the cushion panel 250, to bring the back-side embosses 258 and 260 to contact with each other and to insert the tang portion 256 into the cut 232 from the back side of the blank 200. The side flaps 208 and 210 are folded along the side folding lines 262 and 164 so that when the holder 14 is disposed in the container 12, the side flaps 208 and 210 are positioned substantially parallel to the side panel sections 106 and 108 to damp a shock in the direction parallel to the side panel sections 106 and 108.

The holder 14 thus formed is then inserted into the container 12. Each of the side flaps 208 and 210 includes an aperture 208a and 210a for allowing a finger of an operator to engage the side flap when the holder 14 is disposed in the container 12. Further, in order to facilitate the insertion of the holder 14 in the container 12, each of the side flaps 208 and 210 may include slant edges 208b and 210b at lower portion along at least one of the edges of the side flap. A plurality of glass syringes 20, each of which is sealingly contained in a plastic bag 40, are put into the receiving recesses 230a and 240a. FIG. 1A shows only one glass syringe in a plastic bag 40 held by the holder 14 in the container 12. The side flaps 114 and 116 are folded along the side folding lines 113a and 117a onto the glass syringes held by the supports 230 and 240 to provide the top cushion panel for the glass syringes. The top flap 110 is folded along the upper folding line 111a onto the top cushion panel 114 and 116 as the top wall, and the insert 110a is inserted between the top wall and the front panel section 102. After the top wall 110 is closed, the container 12 with the glass syringes held by the supports 230 and 240 within the container may be sealingly wrapped with a plastic sheet (not shown).

It will also be understood by those skilled in the art that the forgoing description is a preferred embodiment of the disclosed device and that various changes and modifications may be made without departing from the spirit and scope of the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosures of all applications, patents and publications, cited herein and of corresponding Japanese Design application No. 2006-000256, filed Jan. 10, 2005 and Japanese Design Application No. 2006-000257, filed Jan. 10, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A package, comprising:
a rectangular parallelepiped container including vertical front and rear panel sections connected by a pair of vertical side panel sections, a top wall connected to the upper edge of the rear panel section, a bottom wall connected to the at least one of the lower edges of the vertical panels and a top cushion panel disposed beneath the top wall and rotatably connected to at least one of the upper edges of the side panel sections; the top cushion panel including a pair of side flaps connected to the upper edges of the side panel sections, wherein each side flap includes a central folding line extending parallel to the upper edge of the side panel section connected thereto and pairs of reliefs, each pair being symmetrically disposed about the central folding line, the side flaps being folded along the respective central folding lines to provide double-walled halves of the top cushion panel with each pair of reliefs contacting with each other,
a plurality of glass syringes each of which is sealingly contained in a plastic bag; and
a holder, disposed in the container, for holding the plurality of glass syringes substantially parallel to the top and bottom walls and behind the top cushion panel with the top cushion panel overlying all of the glass syringes.

2. A package according to claim 1, wherein the holder includes front and rear side supports in the form of ridges extending in a direction substantially parallel to the front and rear panel sections and having triangular sections, each of the front and rear side supports including a plurality of receiving recesses, the plurality of receiving recesses of the front side support being aligned with the corresponding receiving recesses of the rear side support in a direction perpendicular to the front and rear panel sections.

3. A package according to claim 2 wherein each of the receiving recesses includes a pair of inwardly projecting lugs for engagement with a glass syringe inserted into a receiving recess.

4. A package according to claim 3, wherein each pair of the lugs defines tapered surfaces outwardly diverging relative to each other for facilitating the insertion of the glass syringe into the receiving recess.

5. A package according to claim 2, wherein the holder further includes a rear cushion panel connected to one of the front and rear supports and extending substantially parallel to the rear panel section.

6. A package according to claim 2, wherein the holder further includes a pair of side flaps, connected to the front and rear side supports and extending substantially parallel to the side panel sections of the container, for damping a shock in the direction parallel to the side panel sections.

7. A package according to claim 6, wherein each of the side flaps includes an aperture for allowing a finger of an operator to engage the side flap when the holder is disposed in the container.

8. A package according to claim 6, wherein each of the side flaps includes a slant edge in a lower portion along one of the side edges of the side flap for facilitating the disposition of the holder in the container.

* * * * *